US007972384B2

(12) United States Patent
Parsell

(10) Patent No.: US 7,972,384 B2

(45) Date of Patent: Jul. 5, 2011

(54) AMPUTATION STABILIZATION DEVICE

(76) Inventor: Douglas Eric Parsell, Ridgeland, MS (US)

( * ) Notice: Subject to any disclaimer, the term of this patent is extended or adjusted under 35 U.S.C. 154(b) by 97 days.

(21) Appl. No.: 12/238,108

(22) Filed: Sep. 25, 2008

(65) Prior Publication Data

US 2009/0198342 A1 Aug. 6, 2009

Related U.S. Application Data

(60) Provisional application No. 61/063,570, filed on Feb. 5, 2008.

(51) Int. Cl.
*A61F 2/28* (2006.01)

(52) U.S. Cl. .................................. 623/23.48; 623/16.11

(58) Field of Classification Search ............... 623/23.48, 623/32, 19.11; *A61F 2/28*
See application file for complete search history.

(56) References Cited

U.S. PATENT DOCUMENTS 4,547,912 A 10/1985 Sherva-Parker
4,778,470 A 10/1988 Antebi
4,995,883 A * 2/1991 Demane et al. ............ 623/22.42
5,041,137 A 8/1991 Nemoshkalov
5,314,499 A * 5/1994 Collier, Jr. ...................... 623/47
5,326,365 A 7/1994 Alvine
6,238,434 B1 5/2001 Pappas
6,482,238 B1 11/2002 Grundei
6,709,459 B1 3/2004 Cooney, III et al.
6,923,832 B1 8/2005 Sharkey et al.
7,141,073 B2 11/2006 May et al.
7,223,293 B2 5/2007 Kristensen
2003/0055507 A1* 3/2003 McDevitt et al. .......... 623/19.11
2003/0149485 A1* 8/2003 Tornier ...................... 623/18.11
2005/0049711 A1 3/2005 Ball
2005/0119755 A1 6/2005 Kristensen
2005/0234452 A1 10/2005 Malandain
2006/0015188 A1 1/2006 Grimes
2007/0038302 A1* 2/2007 Shultz et al. ............... 623/19.11
2007/0142917 A1* 6/2007 Roche et al. ............... 623/19.11
2007/0150070 A1 6/2007 Kim et al.
2007/0162150 A1 7/2007 Fago et al.

FOREIGN PATENT DOCUMENTS

DE 3439993 A1 5/1986
DE 4338746 A1 * 5/1995

OTHER PUBLICATIONS

Davids, et al., "Operative treatment of bone overgrowth in children who have an acquired of congenital amputation" The Journal of Bone and Joint Surgery, vol. 77-A. No. 10., Oct. 1995, 1490-1497. Bernd, et al., "The Autologous Stump Plasty Treatment for Bony Overgrowth in Juvenile Amputees", The Journal of Bone and Joint Surgery [Br.], vol. 73-B, No. 2, Mar. 1991, 203-206.

* cited by examiner

*Primary Examiner* — David Isabella
*Assistant Examiner* — Jason-Dennis Stewart
(74) *Attorney, Agent, or Firm* — Workman Nydegger

(57) ABSTRACT

The present invention extends to a stemmed amputation implant. In some embodiments, a dual stemmed implant includes a base plate and two intramedullary rods extending from the proximal side of the base plate. The two intramedullary rods are configured for insertion into corresponding intramedullary bone canals reamed into remaining portions of amputated bones, such as, for example, a tibia and fibula or an ulna and radius. The position of the intramedullary rods relative to one another is configured to maintain appropriate separation between amputated bones when the first intramedullary rod and the second intramedullary rod are inserted into the amputated bones. In some embodiments, a hollow tube replaces one or more of the intramedullary rods. A hollow tube can be configured to cover the exterior of a bone, such as, for example, the fibula, when the bone is not stable enough for intramedullary fixation.

31 Claims, 11 Drawing Sheets

Amputated Fibula 122
Amputated Tibia 121
Intramedullary Bone Canal 123
Intramedullary Bone Canal 124
Intramedullary Rod 101
Intramedullary Rod 102
134 Proximal Side
Base Plate 103
136 Distal Side

AMPUTATION STABILIZATION DEVICE

CROSS-REFERENCE TO RELATED APPLICATIONS

This application claims the benefit of U.S. Provisional Application No. 61/063,570, entitled "Dual Stem Amputation Implant", filed on Feb. 5, 2008, which is incorporated herein in its entirety.

BACKGROUND

Background and Relevant Art

A human being's loss of a limb or portion thereof is most often an acquired condition resulting from amputation. Amputation of a limb or portion thereof can result from physical injury or can be performed as treatment for a physical injury or disease. Amputation can be used as treatment for physical injury when an extremity is so severely damaged that the extremity's recovery is unlikely and the extremity's continued attachment to the body would cause further medical complications. Amputations can also be used to treat a number of diseases, such as, for example, peripheral vascular disease ("PVD"), diabetes, blood clots, and bone infections (e.g., osteomyelitis), when disease prevents proper function of an extremity and recovery is unlikely. Portions of limbs can also be amputated when removing tumors from bones and muscles. Congenital limb deficiency can also occur when an infant is born without all or part of a limb.

Treatment for individuals that lack a limb or portion thereof often include the use of a prosthesis. A prosthesis is an artificial extension that replaces a missing body part. Depending on the level and type of amputation a prosthesis can provide varied levels of benefit to an individual. For example, individuals who receive below the knee amputations ("BKA") of the tibia and fibula function fairly well with a properly fit prostheses and functioning knee joints. However, physical pain is common for these individuals at the anteriodistal bone ends of the amputation when loaded heavily. The source of the pain is often a combination of one or more of: tissue compression at the bone ends, pressure applied to soft tissue/bone end adhesions, and bone end motion. Bone end motion (or "chop-sticking") results because the tibia and fibula are no longer connected on the distal end and can move independently of one another.

Ideally fit prostheses attempt to reduce this pain by redistributing virtually all of the bone end loading to the soft tissues around the calf However, these tissues are not anatomically designed to bear these additional loads. Thus, other physical problems can result from these loads, such as, for example, soft tissue swelling, loss of bone density, and soft tissue necrosis.

BRIEF SUMMARY

The present invention extends to an amputation stabilization device. In some embodiments, a dual stemmed amputation implant includes a first intramedullary rod and a second intramedullary rod. The first intramedullary rod is configured for insertion into the distal end of the tibia of an amputated leg. The second intramedullary rod is configured for insertion into the distal end of the fibula of the amputated leg. The dual stem implant also includes a base plate having a proximal side and a distal side.

The base plate is mechanically connected to the first intramedullary rod and to the second intramedullary rod. The first and second intramedullary rods extend out of the proximal side of the base plate. The position of the mechanical connection of the first intramedullary rod on the base plate relative to the position of mechanical connection of the second intramedullary rod on the base plate is configured to maintain appropriate separation between the tibia and fibula when the first intramedullary rod and the second intramedullary rod are inserted into corresponding intramedullary canals of the tibia and fibula respectively.

Other embodiments include first and second intramedullary rods configured for insertion into the ulna and radius of an amputated fore arm.

Further embodiments include first and/or second hollow tubes. A hollow tube is configured to cover the exterior of a bone, such as, for example, the fibula, when the bone is not stable enough for intramedullary fixation. Thus, embodiments include stemmed implants with one intramedullary rod and one hollow tube as well as amputation stabilization devices with two hollow tubes.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

The present invention extends to an amputation stabilization device. In some embodiments, a dual stemmed amputation implant includes a first intramedullary rod and a second intramedullary rod. The first intramedullary rod is configured for insertion into the distal end of the tibia of an amputated leg. The second intramedullary rod is configured for insertion into the distal end of the fibula of the amputated leg. The dual stem implant also includes a base plate having a proximal side and a distal side.

The base plate is mechanically connected to the first intramedullary rod and to the second intramedullary rod. The first and second intramedullary rods extend out of the proximal side of the base plate. The position of the mechanical connection of the first intramedullary rod on the base plate relative to the position of mechanical connection of the second intramedullary rod on the base plate is configured to maintain appropriate separation between the tibia and fibula when the first intramedullary rod and the second intramedullary rod are inserted into corresponding intramedullary canals of the tibia and fibula respectively.

Other embodiments include first and second intramedullary rods configured for insertion into the ulna and radius of an amputated fore arm.

Further embodiments include first and/or second hollow tubes. A hollow tube is configured to cover the exterior of a bone, such as, for example, the fibula, when the bone is not stable enough for intramedullary fixation. Thus, embodiments include stemmed implants with one intramedullary rod and one hollow tube as well as amputation stabilization devices with two hollow tubes.

Accordingly, embodiments of the invention include an implantable device (e.g., a below the knee amputation ("BKA") implant) that is mechanically fixed to both of the terminal ends of an amputated tibia and fibula bones. The implantable device provides mechanical stabilization of remaining portions of the tibia and fibula. The implantable device also provides an expanded terminal (distal) surface area for soft tissue weight bearing.

Figure 1A:
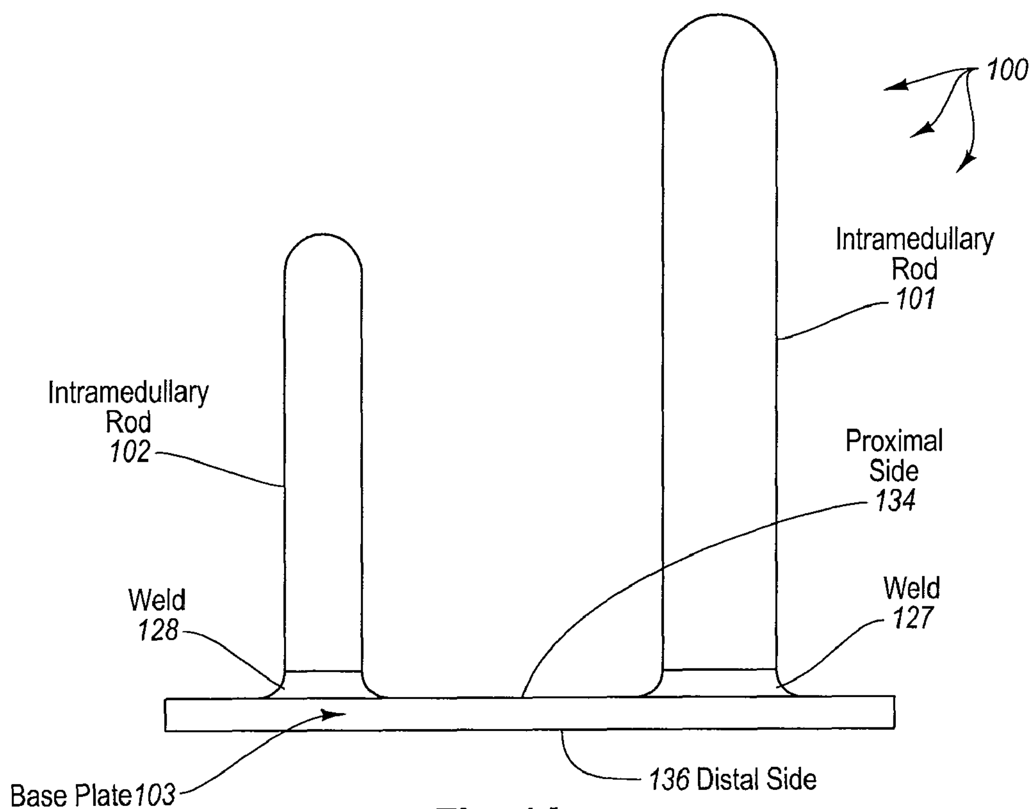
FIG. 1A illustrates an example of a dual stem implant.

In some embodiments, an amputation stabilization device includes a base plate and two intramedullary rods. For example, referring to FIG. 1A, FIG. 1A depicts an example of dual stem implant 100. Dual stem implant 100 includes intramedullary rod 101, intramedullary rod 102, and base plate 103.

Base plate 103 can be constructed of a smooth, mechanically tough material, such as, for example, ultra high molecular weight polyethylene ("UHMWPE"), stainless steel, titanium based alloy, or cobalt-chrome based alloy. Base plate 103 can be shaped in a pressure-reducing configuration, such as, for example, a moderately flattened domed shape. The moderately flattened dome can be backed with a reinforcing metal substrate. The metal substrate can be of a solid, non-porous configuration.

Alternatively the metal substrate can be surfaced with a highly porous material of significant strength, such as, for example, a porous metallic material. The porous layer permits newly generated bone to infiltrate from the terminal bone ends. Thus, in some embodiments, base plate 103 is a tough, dome-shaped, pressure reducing surface backed with a reinforcing metal shell that is further backed with a porous, bone infiltratable material.

The shape of the base plate 103 can be anatomically matched to the cross section (or remaining area) of the tibia and fibula at the particular level of amputation. Alternatively, the base plate 103 can be of a size somewhat larger than the cross section of the associated bones, so as to provide a greater area of load bearing for the distal soft tissues during ambulation.

As depicted, base plate 103 includes a proximal side 134 (facing towards amputated bones) and distal side 136 (facing away from amputated bones). Extending out from proximal side 134 are intramedullary rods 101 and 102. Intramedullary rods 101 and 102 are mechanically connected to the proximal side of base plate 103. Intramedullary rods 101 and 102 can be mechanically connected to base plate 103 using any of a variety of techniques, such as, for example, welding, screw threads, adhesives, etc. As depicted in FIG. 1A, welds 127 and 128 mechanically connect intramedullary rods 101 and 102 respectively to base plate 103. Intramedullary rods 101 and 102 may or may not be substantially parallel to one another depending on the type and level of amputation.

Intramedullary rod 101 is configured for insertion into the distal end of an amputated tibia. For example, the diameter of intramedullary rod 101 can be matched to a corresponding intramedullary bone canal of the amputated tibia. Intramedullary rod 102 is configured for insertion into the distal end of an amputated fibula. For example, the diameter of intramedullary rod 102 can be matched to a corresponding intramedullary bone canal of the amputated fibula.

The surface of the intramedullary rods 101 and 102 may be smooth or textured so as to permit the ingrowth of bone. In some embodiments, the surfaces include porous textured (e.g., metallic) materials. The ends of intramedullary rods 101 and 102 can be bluntly rounded so as to facilitate safe egress into corresponds intramedullary bone canals. The cross-sectional profile of the intramedullary rods 101 and 102 can be circular. Alternately, intramedullary rods 101 and 102 can be of a shape with a higher aspect ratio to aid in mechanical anti-rotation control.

Figure 1B:
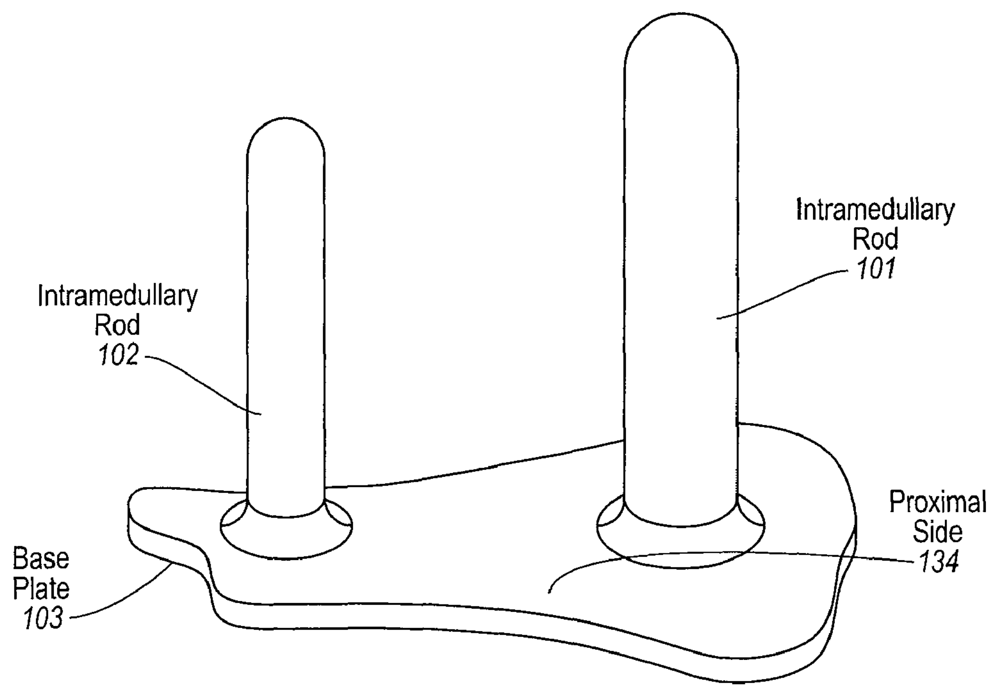
FIG. 1B illustrates a perspective view of the dual stem implant of FIG. 1A.

FIG. 1B depicts a perspective view of dual stem implant 100. As depicted, intramedullary rods 101 and 102 extend out of proximal side 134 of base plate 103.

The length of intramedullary rod 101 and intramedullary rod 102 can be configured to maximize their insertion into the intramedullary bone canals of an amputated tibia and fibula. The position of intramedullary rod 101 and intramedullary rod 102 can also be configured to maximize their insertion into the intramedullary bone canals of the amputated tibia and fibula. Further, the position of intramedullary rod 101 relative to intramedullary rod 102 can be used to maintain appropriate separation between the remaining portion of an amputated tibia and the remaining portion of an amputated fibula after insertion. Accordingly, altering the lengths of intramedullary rods 101 and 102 and/or the position of the mechanical connection of intramedullary rod 101 on base plate 103 relative to the position of the mechanical connection of intramedullary rod 102 on the base plate 103 provides clinical flexibility.

Figure 1C:
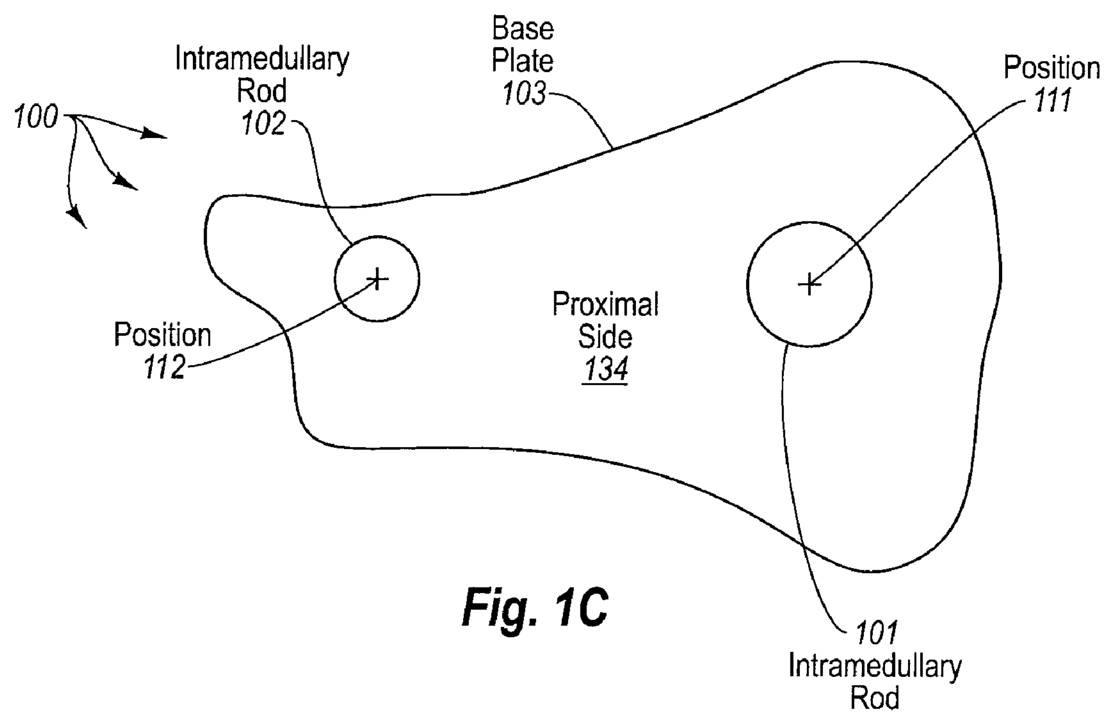
FIG. 1C illustrates a top view of the dual stem implant of FIG. 1A.

FIG. 1C depicts a top view of dual stem implant 100. As depicted, positions 111 and 112 indicate the location for mechanical connections between intramedullary rods 101 and 102 respectively and base plate 103. Positions 111 and 112 can be varied to provide increased patient benefit based on the level and type of amputation.

Figure 1D:
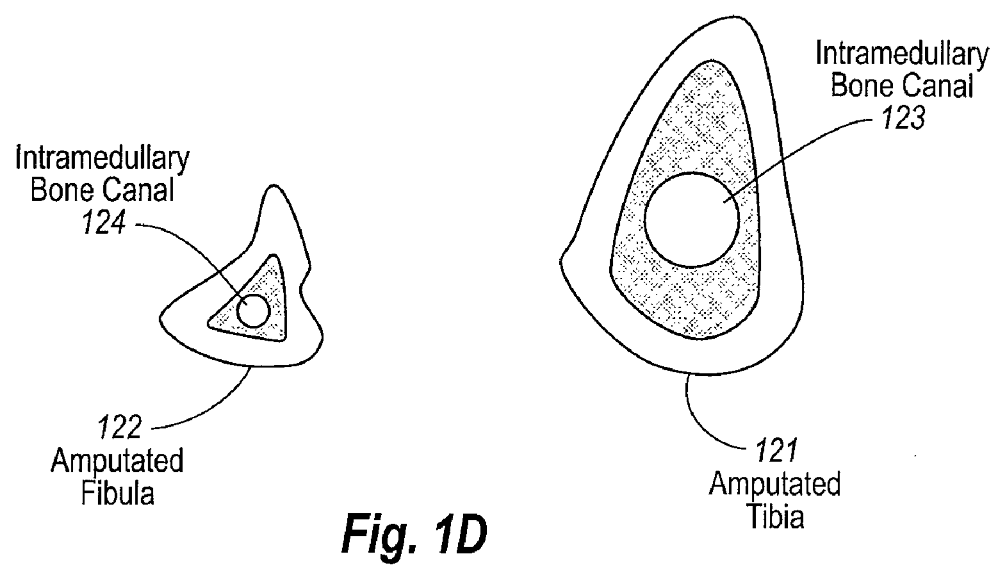
FIG. 1D illustrates a distal view of intramedullary bone canals in an amputated tibia and fibula respectively.

FIG. 1D depicts a distal view of intramedullary bone canals in an amputated tibia 121 and amputated fibula 122 respectively. As depicted, amputated tibia 121 and fibula 122 include intramedullary bone canals 123 and 124 respectively. Intramedullary bone canals can be formed in the amputated tibia 121 and amputated fibula 122 using a surgical reaming tool.

Figure 1E:
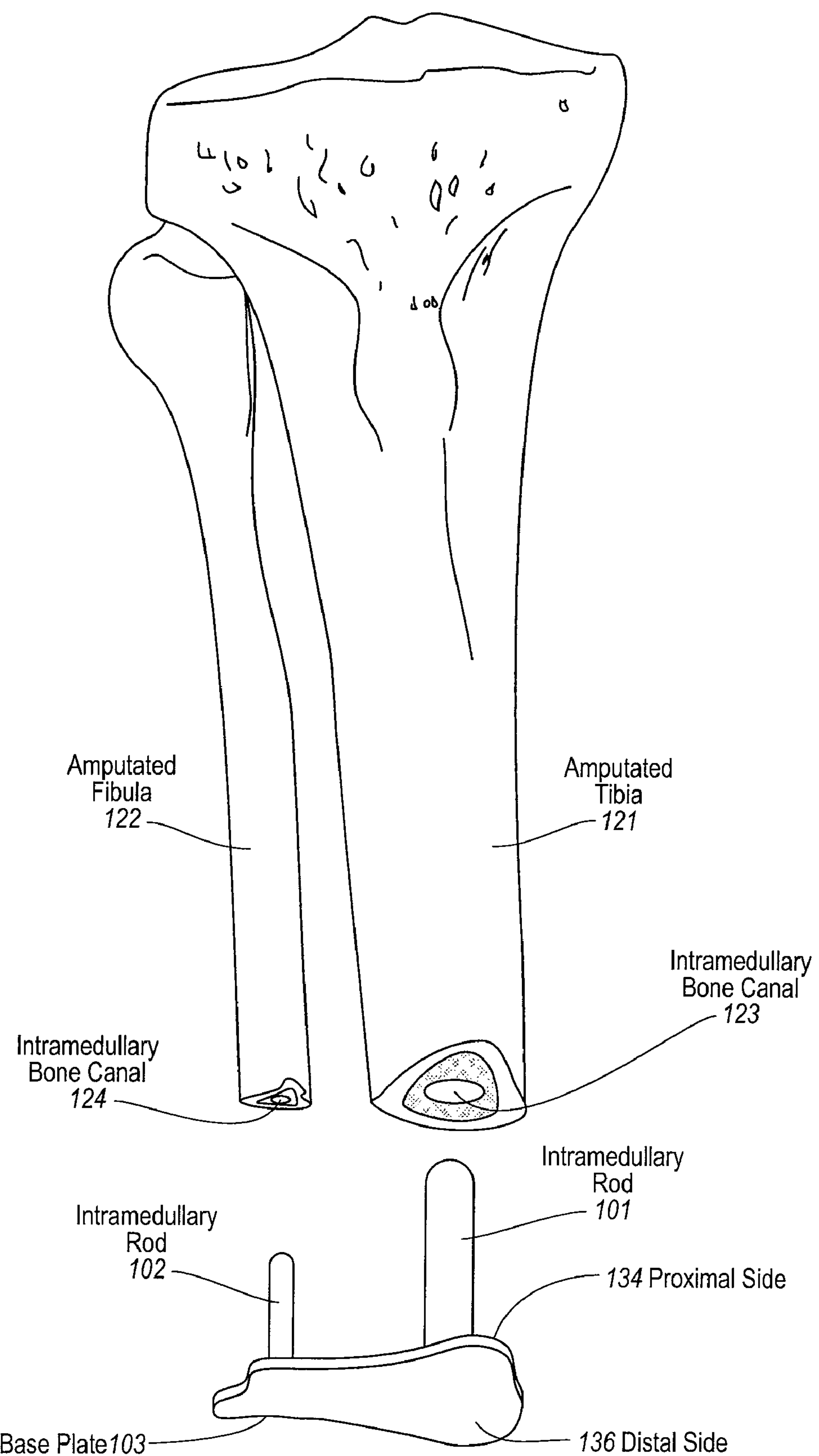
FIG. 1E illustrates a view of the dual stem implant of FIG. 1A relative to the amputated tibia and fibula of FIG. 1D.

Connection of the base plate 103 and intramedullary rods 101 and 102 to an amputated tibia and fibula can be facilitated using orthopedic fixation methods. In some embodiments, intramedullary rods are inserted into intramedullary bone canals. FIG. 1E depicts a view of dual stem implant 100 relative to amputated tibia 121 and amputated fibula 122. As depicted in FIG. 1E, intramedullary rods 101 and 102 can be inserted into intramedullary bone canals 123 and 124 respectively. Attachment of intramedullary rods 101 and 102 to amputated tibia 121 and amputated fibula 122 respectively can result in a (e.g., relatively intimate) fit between a porous textured (e.g., metallic) rod surface and corresponding intramedullary bone canal. The attachment can facilitate bone growth into the porous textured surface.

Alternatively, an intentional gap can be formed between an intramedullary rod and corresponding intramedullary bone canal. The canal can provide adequate space for the mechanical bonding of an intermediate layer of bone cement. Typical bone cements used for orthopedic implant fixation, such as, for example, those based upon PMMA chemistries, can be used.

Insertion of higher aspect ratio intramedullary rods can include a multi-step reaming system configured to yield the desired stem cross-section shape.

In some embodiments, insertion of dual stem implant 100 into amputated bone ends is complete when the inner surface of the base plate 103 securely contacts the amputated surface of the amputated tibia and fibula. Dual intramedullary rods (e.g., 101 and 102) are stabilized to the bone shafts via press fit mechanisms or cementation. Alternatively, rod fixation is through insertion of bicortical distal locking screws.

Figure 1F:
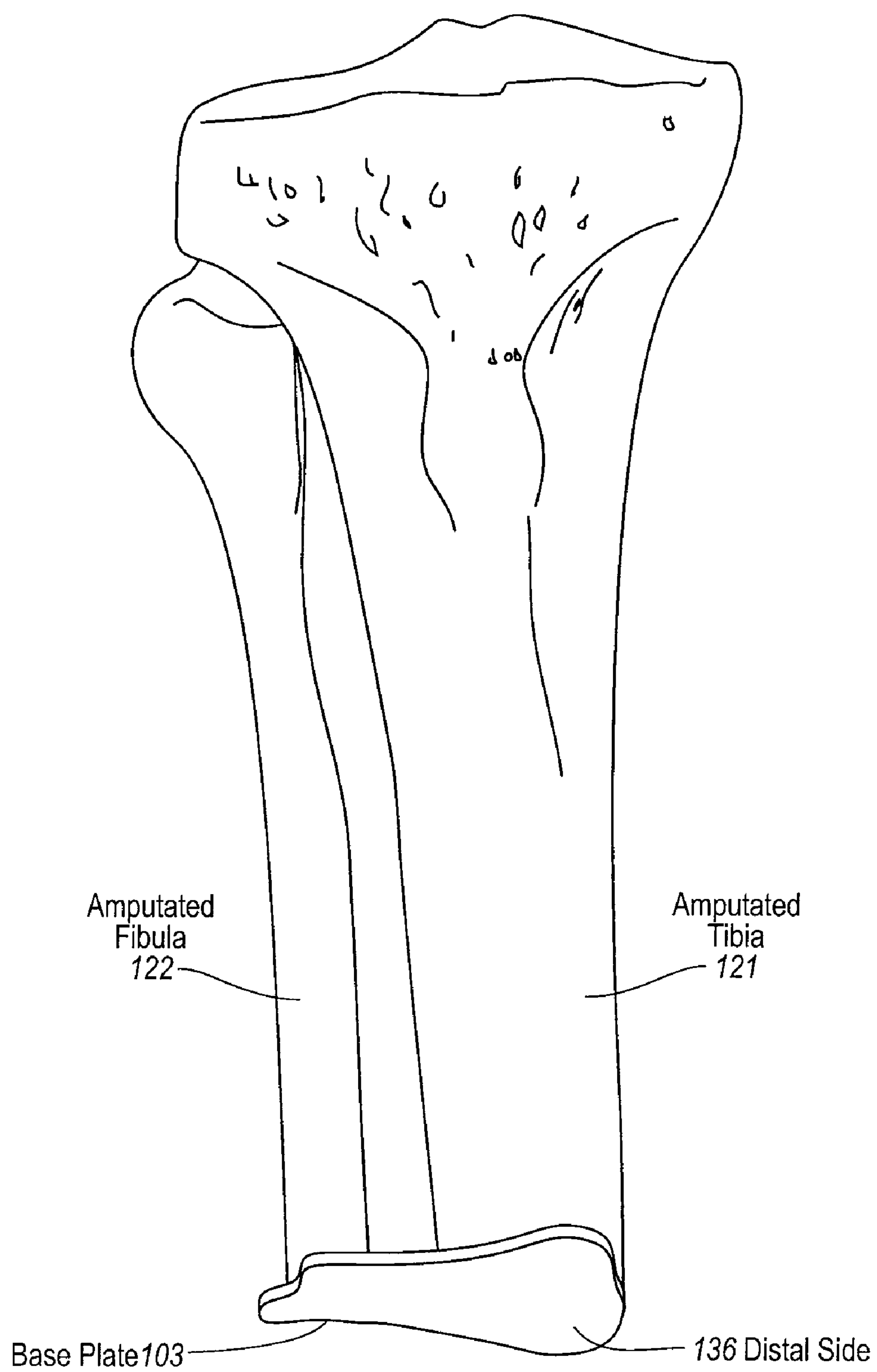
FIG. 1F illustrates a view of the dual stem implant device of FIG. 1A inserted into the amputated tibia and fibula of FIG. 1D.

FIG. 1F depicts a view of the dual stem implant 100 inserted into the amputated tibia 121 and amputated fibula 122. Appropriate insertion of dual stem implant 100 and fixation of intramedullary rods 101 and 102 significantly decreases any independent movement of amputated tibia 121 and amputated fibula 122 relative to one another. Reducing independent movement of amputated tibia 121 and amputated fibula 122 can result in a corresponding decrease in patient pain levels.

As previously described, intramedullary rods can be mechanically connected to a base plate using any of a variety of mechanisms. Thus, a dual stem implant can be configured (and pre-designed for a specific patient) as a single piece wherein the base plate and rods securely attached to each other via casting or welding manufacturing operations. Alternatively, the base plate and intramedullary rods may be presented as separate entities. Accordingly, a surgical team is given additional clinical flexibility to select from various base plate dimensions, stem lengths, stem diameters and base plate surface preparations and stem surface preparations to optimally match the clinical situation.

On site attachment of intramedullary rods to a base plate may be via screwing a distally threaded stem into a correspondingly threaded (proximal) base plate receiving hole.

Figure 2A:
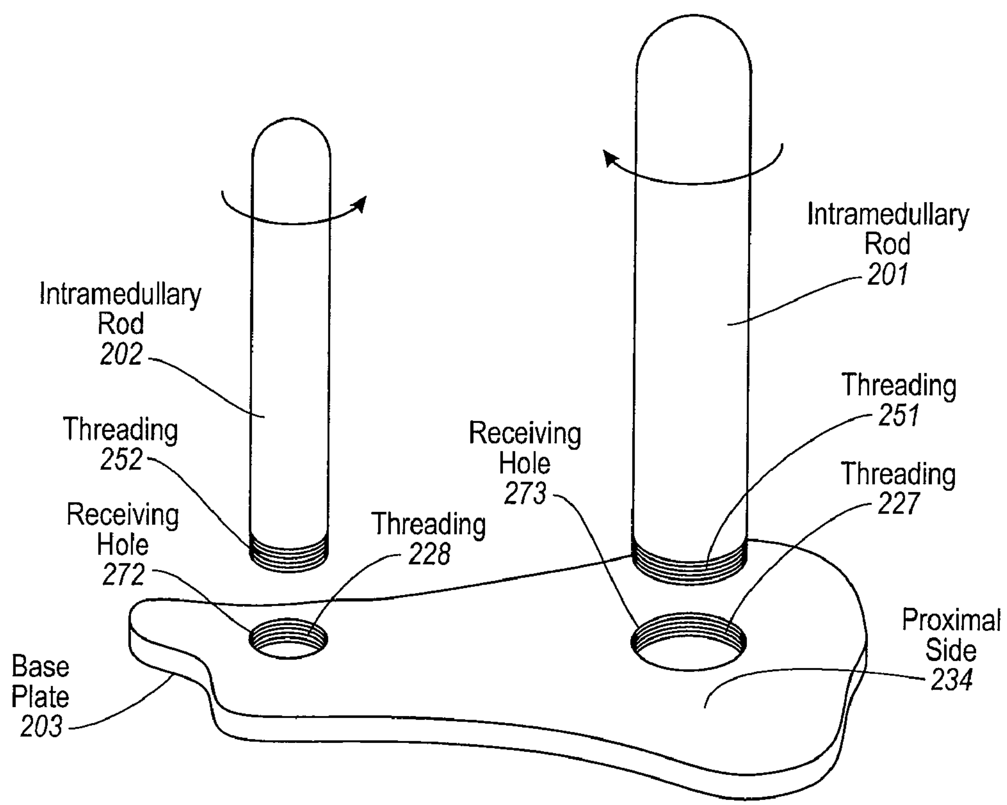
FIG. 2A illustrates threaded intramedullary rods relative to a threaded baseplate.

FIG. 2A depicts threaded intramedullary rods 201 and 202 relative to threaded base plate 203. As depicted, base plate 203 includes receiving holes 272 and 273. Receiving hole 272 includes threading 228 that is configured to match threading 252 of intramedullary rod 202. Likewise, receiving hole 273 includes threading 227 that is configured to match threading 251 of intramedullary rod 201.

Figure 2B:
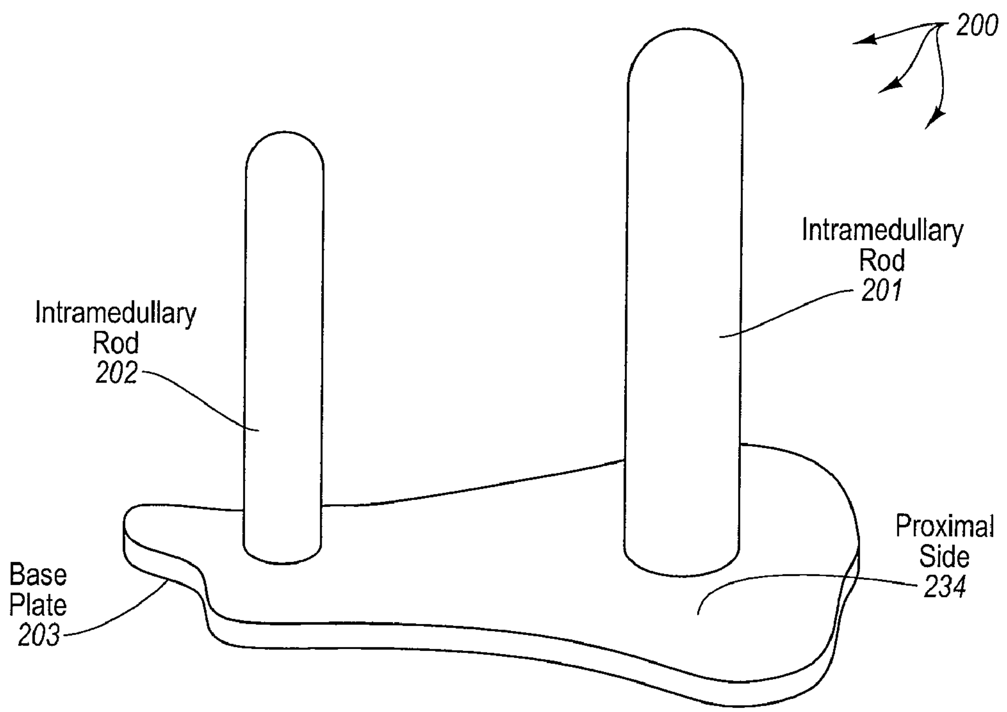
FIG. 2B illustrates the threaded intramedullary rods of FIG. 2A screwed into the threaded base plate of FIG. 2A.

As such, intramedullary rod 201 can be screwed into receiving hole 273 to mechanically connect intramedullary rod 201 to base plate 203. Similarly, intramedullary rod 202 can be screwed into receiving hole 272 to mechanically connect intramedullary rod 202 to base plate 203. FIG. 2B depicts intramedullary rods 201 and 202 screwed into receiving holes 273 and 272 respectively of base plate 203 to form dual stem implant 200.

Deformable inserts can be used to minimize unwanted backing out of threaded components. Additional, contrasting threading directions (a right-handed tibial stem and a left-handed fibular stem) can be utilized to further inhibit unwanted component backing out.

Figure 3A:
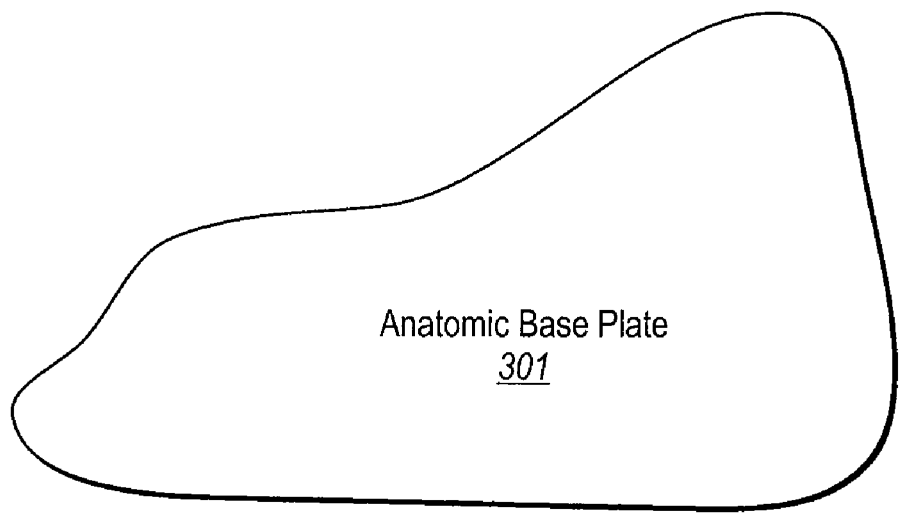
FIG. 3A illustrates an example of a base plate.

As previously described, the cross-sectional of a base plate can vary for different applications. FIG. 3A depicts an example of an anatomic base plate 301. Anatomic base plate 301 can be configured to extend to, or essentially anatomically match up with, the edges of the distal end of an amputated tibia and fibula (e.g., as depicted in FIG. 1F).

Figure 3B:
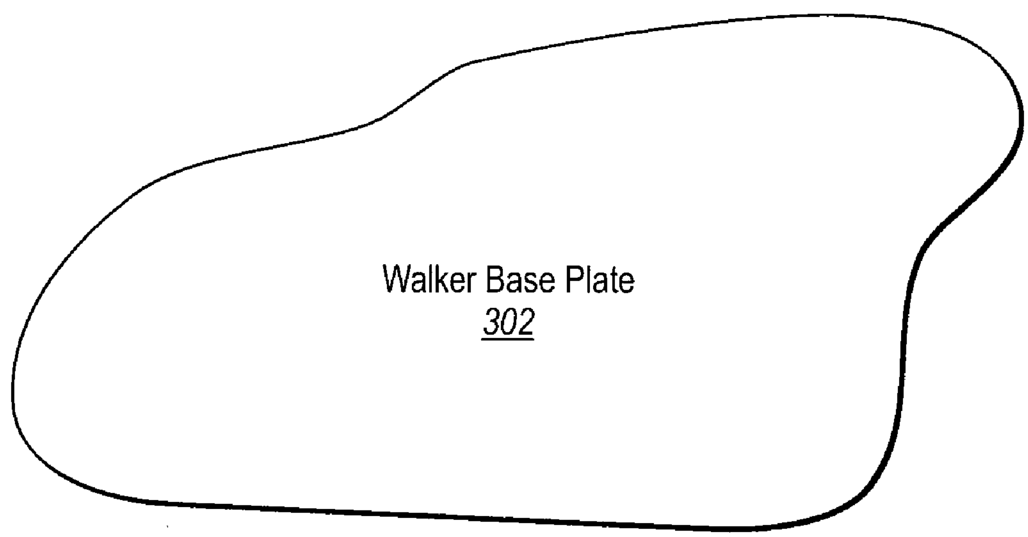
FIG. 3B illustrates an example of a base plate.

FIG. 3B depicts an example of a walker base plate 302. Walker base plate 302 is configured to extend significantly past the edges of the distal end of an amputated tibia and fibula in one or more locations. Walker base plate 302 provides increased lateral surface area in the front portion to better distribute concentrated loads, such as, for example, experienced during toe off phase ambulation. Walker base plate 302 can provide significant more bearing surface (e.g., approximately a 50% increase) than anatomic base plate 301.

Figure 4A:
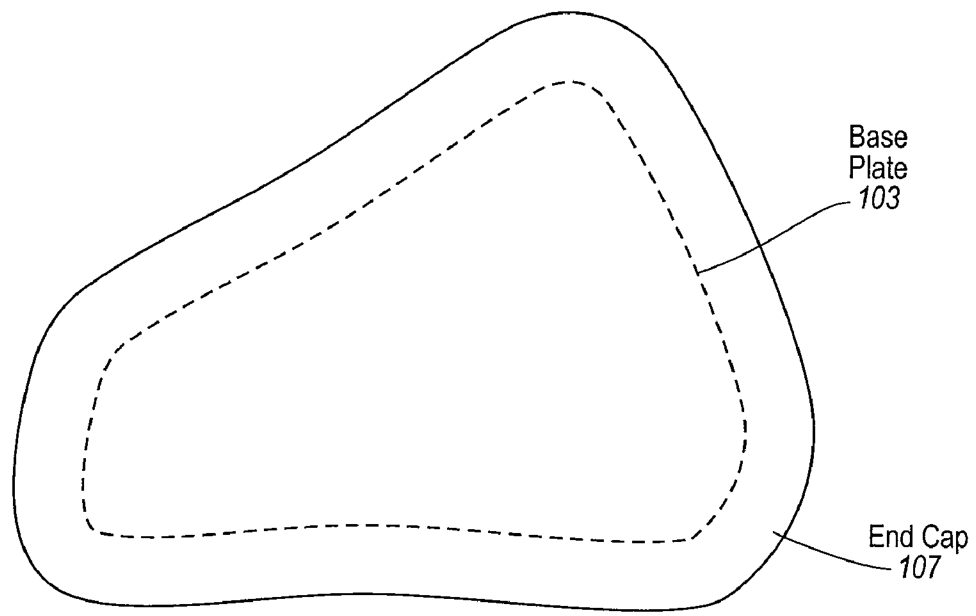
FIG. 4A illustrates an example of an end cap.

In some embodiments, an end cap of softer material is affixed to the distal side of a base plate prior to or subsequent to insertion of a dual stem implant into amputated bone ends. FIG. 4A depicts an example of end cap 107. End cap 107 can be made of a plastic or other polymer composition. End cap 107 provides a mechanism to further distribute concentrated loads. End cap 107 can be designed for use with any configuration of base plate. Accordingly, end cap 107 can be configured for use with anatomical base plates as well as walker base plates.

Figure 4B:
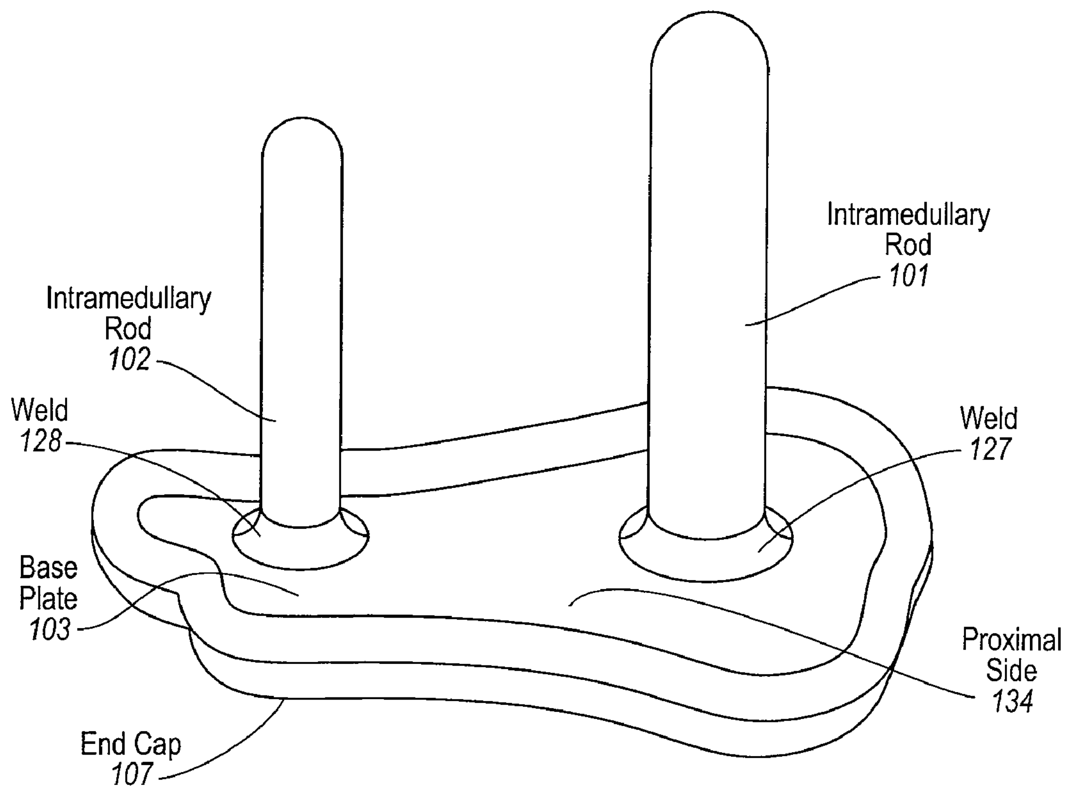
FIG. 4B illustrates the end cap of FIG. 4A connected to the dual stem implant of FIG. 1A.
Figure 4C:
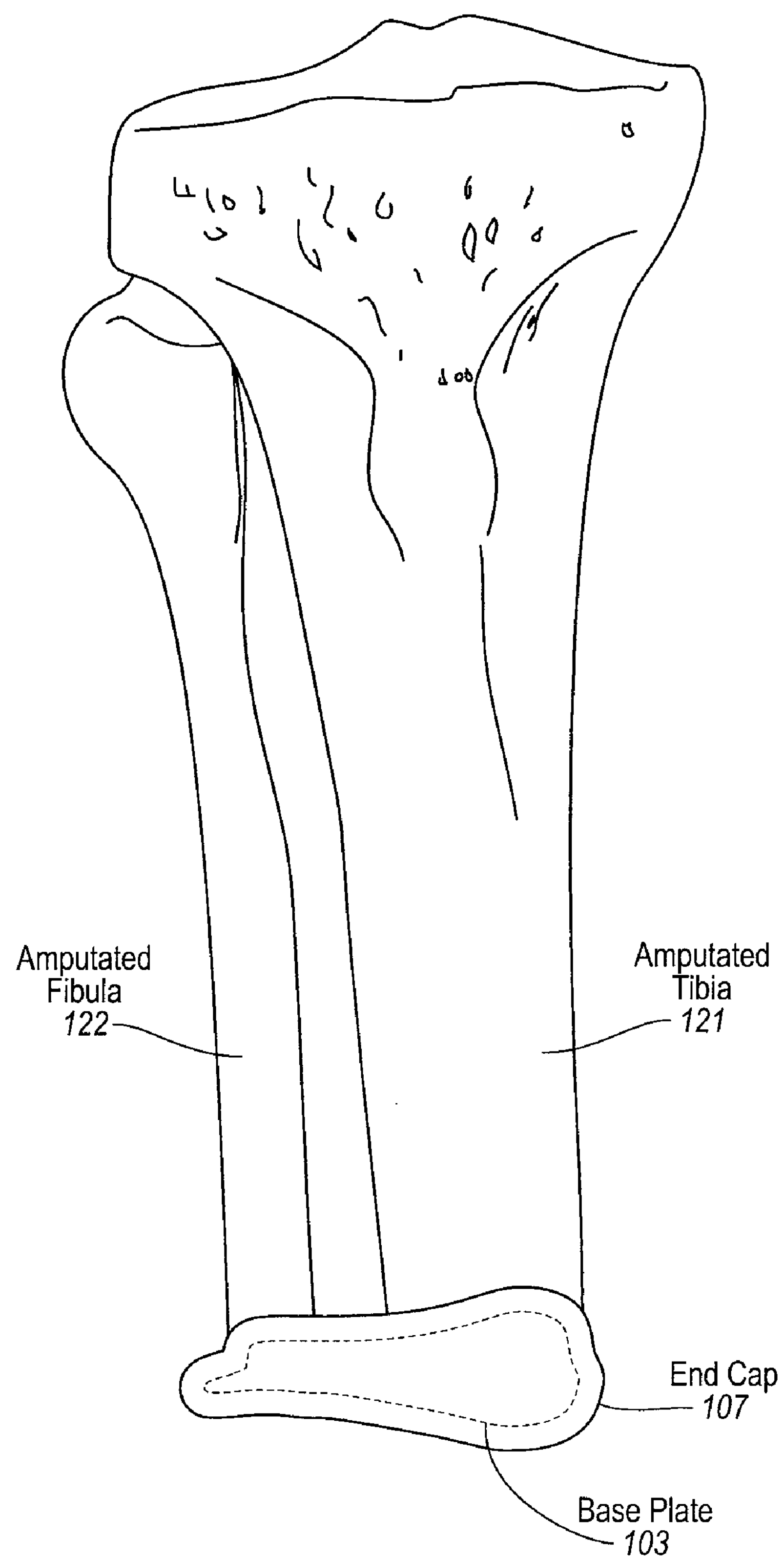
FIG. 4C illustrates a view of the dual stem implant device and end cap of FIG. 4B inserted into an amputated tibia and fibula.

FIG. 4B depicts end cap 107 affixed to the proximal side of dual steam implant 100. FIG. 4C illustrates dual stem implant 100, with end cap 107 affixed, inserted into amputated tibia 121 and amputated fibula 122. End cap 107 can be affixed to base plate 103 using adhesives or other attachment mechanisms.

Figure 5A:
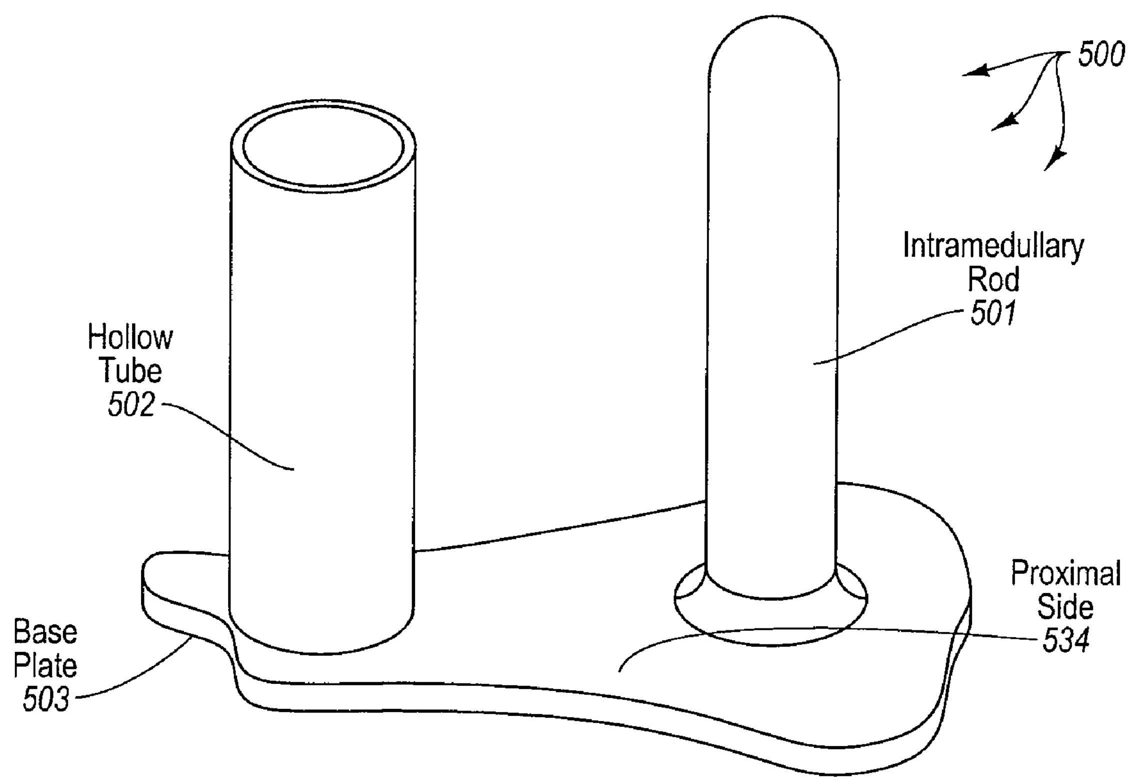
FIG. 5A illustrates another example of a stemmed implant, including a hollow tube.

In other embodiments, an amputation stabilization device includes one or more hollow tubes. For example, a hollow tube can be used in a stemmed implant to replace an intramedullary rod. FIG. 5A depicts stemmed implant 500 including intramedullary rod 501 and hollow tube 502. Hollow tube 502 can be constructed using any material and/or construction technique used to construct an intramedullary rod. Hollow tube 502 can be mechanically connected to base plate 503 using any of the mechanisms for mechanically connecting an intramedullary rod to base plate 503. Stemmed implant 500 can be used, for example, when the cross-sectional area of an amputated bone (e.g., an amputated fibula) does not provide sufficient size for stable intramedullary fixation. Intramedullary rod 501 and hollow tube 502 may or may not be substantially parallel to one another depending on the type and level of amputation.

Figure 5B:
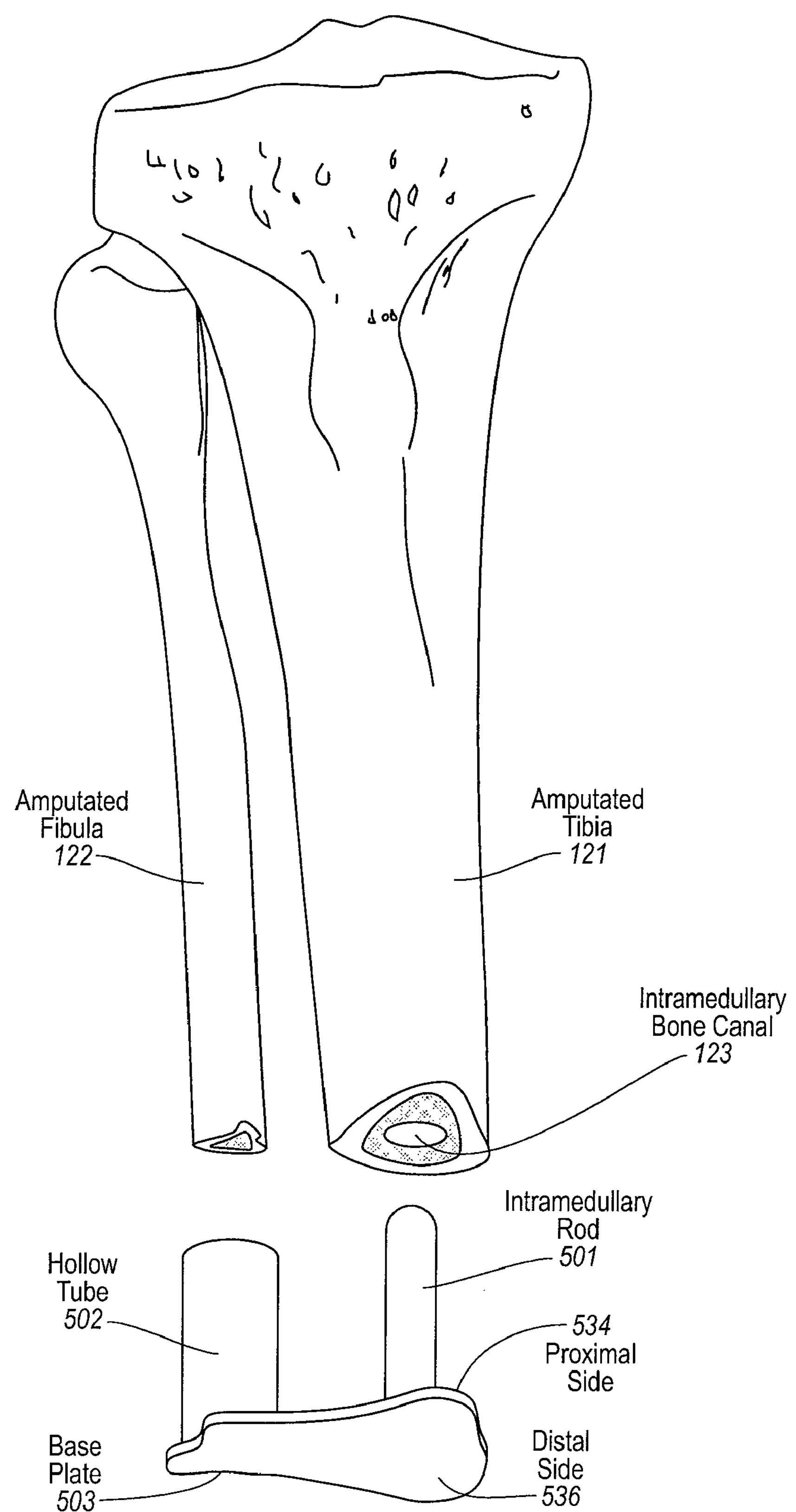
FIG. 5B illustrates a view of the stemmed implant of FIG. 5A relative to an amputated tibia and fibula.

In some embodiments, hollow tube 502 has a circular cross section. The diameter of hollow tube 502 can be selected to be slightly larger than the maximum diameter of an amputated bone for a given amputation level. FIG. 5B depicts stemmed implant 500, including hollow tube 502, relative to amputated tibia 121 and amputated fibula 122. As depicted, hollow tube 502 is of sufficient size to fit over the outside of amputated fibula 122 during insertion of intramedullary rod 501 into intramedullary bone canal 123.

Figure 5C:
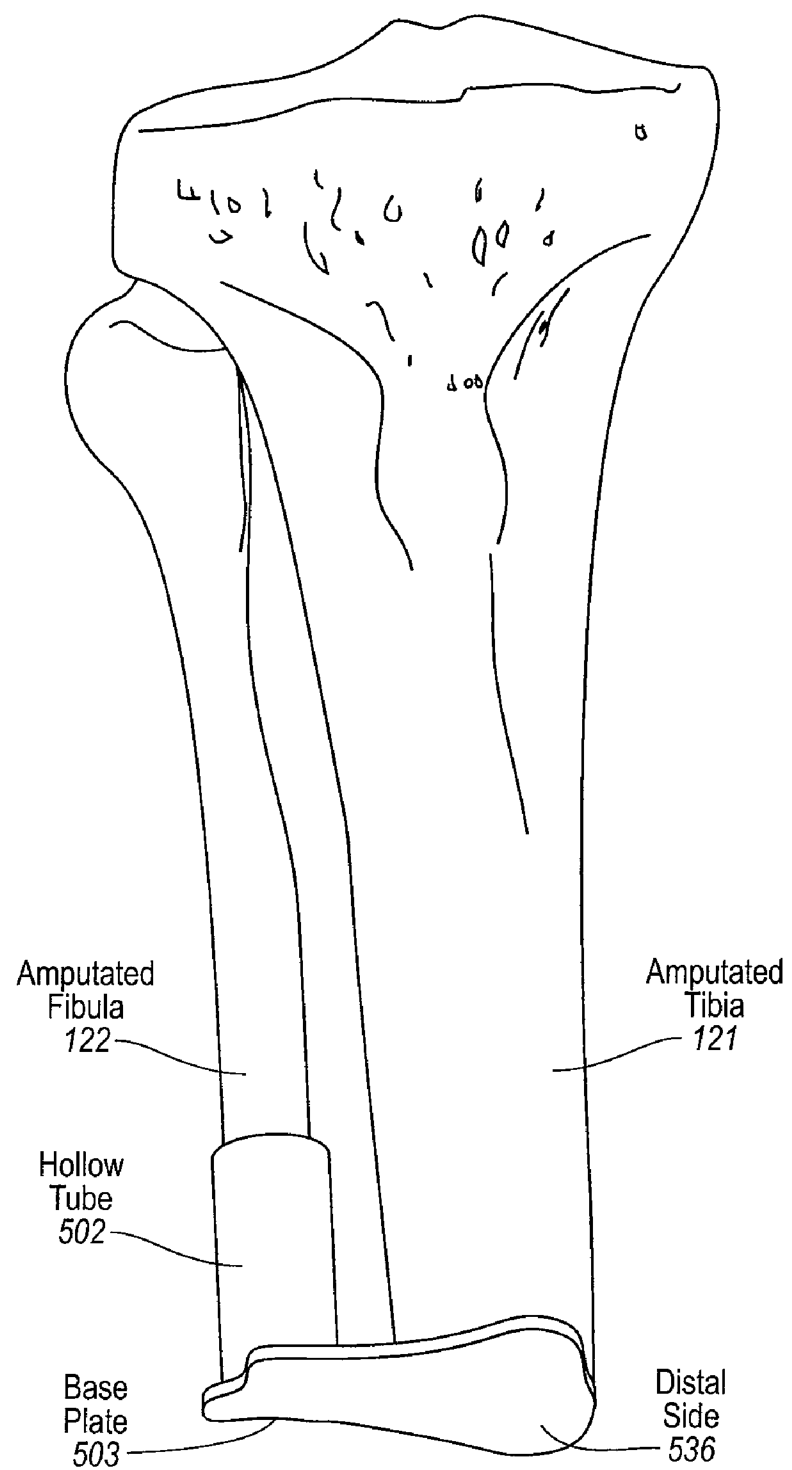
FIG. 5C illustrates a view of the stemmed implant device of FIG. 5A attached to the amputated tibia and fibula of FIG. 5B.

FIG. 5C depicts stemmed implant 500 attached to the amputated tibia 121 and amputated fibula 122. Mechanical retention of a remaining portion of an amputated bone (e.g., amputated fibula 122) within hollow tube 502 can be facilitated using orthopedic attachment techniques including, for example, orthopedic bone cements and screws. An end cap, such as, for example, end cap 107 can also be attached to stemmed implants including hollow tubes.

In further embodiments, an amputation stabilization device includes two hollow tubes. The hollow tubes may or may not be substantially parallel to one another depending on the type and level of amputation.

Embodiments of the invention also include amputation stabilization devices for the radius and ulna of an amputated forearm. These embodiments can be dual stemmed devices, stemmed implants including a hollow tube, or amputation stabilization devices including two hollow tubes. End caps, such as, for example, end cap 107 can also be used with these embodiments when appropriate. In these forearm related embodiments, first and second intramedullary rods, an intramedullary rod and a hollow tube, or first and second hollow tubes, can be configured relative to and positioned on a base plate to provide for proper biomechanics when the user rotates their wrist and/or forearm.

Amputation stabilization devices configured in accordance with the principals of the of the present invention can be supported by a host of devices used in the field of orthopedic implant surgery, such as, for example, within the subspecialty of total joint arthroplasty. Devices can include cutting guides, reaming guides, combination cutting/reaming guides, intramedullary reamers, sterile bone cements, bone cement mixing equipment and bone cement extruding equipment.

Advantageously, embodiments of the invention reduce the occurrence of soft tissue/bone end adhesions by covering the interface between the two types of tissues with a biologically inert material. Embodiments of the invention also reduce the occurrence of "chop sticking" through prevention of independent bone movement.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed:

1. An amputation stabilization device for mechanically stabilizing a remaining end of a tibia relative to a remaining end of a fibula of a partially amputated leg, the amputation stabilization device comprising:

a first stabilizing component configured for connection to a remaining end of a tibia of a partially amputated leg;

a second stabilizing component configured for connection to a remaining end of a fibula of a partially amputated leg; and a base plate having a proximal side and a distal side, a first region of the base plate to which the first stabilizing component is mechanically connected or connectable, and a second region of the base plate to which the second stabilizing component is mechanically connected or connectable, wherein the first region has a first irregular, non-symmetrical shape that approximates a remaining cross section of a tibia, wherein the second region has a second irregular, non-symmetrical shape that is different than the first shape and that approximates a remaining cross section of a fibula, and wherein the base plate has an irregular, non-symmetrical shape that approximates a remaining cross-section of a partially amputated leg;

wherein the first stabilizing component is configured to extend from the proximal side of the base plate in the first region;

wherein the second stabilizing component is configured to extend from the proximal side of the base plate in the second region; and wherein during use of the amputation stabilization device the first stabilizing component has a position on the base plate relative to a position of the second stabilizing component on the base plate in order to maintain an anatomically correct separation between remaining ends of a tibia and a fibula when the first stabilizing component and the second stabilizing component are connected to the remaining ends of a tibia and a fibula, respectively, and wherein the amputation stabilization device is configured to decrease independent movement of a tibia relative to a fibula of a partially amputated leg during dynamic loading of the partially amputated leg.

2. The amputation stabilization device as recited in claim 1, wherein the first stabilizing component has a size based on a size and shape of a remaining cross-section of a tibia, wherein the second stabilizing component has a size that is less than the size of the first stabilizing component and is based on a size and shape of a remaining cross-section of a fibula.

3. The amputation stabilization device as recited in claim 1, wherein the first stabilizing component comprises a first intramedullary rod having a diameter configured for insertion into an intramedullary bone canal of a tibia of a partially amputated leg, and wherein the second stabilizing component comprises a second intramedullary rod having a diameter that is less than the diameter of the first intramedullary rod and configured for insertion into an intramedullary bone canal of a fibula of a partially amputated leg.

4. The amputation stabilization device as recited in claim 3, wherein the first intramedullary rod has a first threaded portion extending from a non-flared proximal end of the first intramedullary rod, the first threaded portion having a first diameter and being configured to be screwable into a first correspondingly sized threaded hole in the first half of the base plate, wherein the second intramedullary rod has a second threaded portion extending from a non-flared proximal end of the second intramedullary rod, the second threaded portion having a second diameter that is less than the first diameter of the first threaded portion and being configured to be screwable into a second correspondingly sized threaded hole in the second region of the base plate that is smaller than the first threaded hole in order to prevent the first threaded portion to be screwed into the second threaded hole and prevent the second threaded portion to be screwed into the first threaded hole.

5. The amputation stabilization device as recited in claim 1, further comprising:

an end cap mechanically attached to the distal side of the base plate, the end cap configured to cover the distal side the base plate and provide a substantially flat or curved distal surface, the end cap comprising a less rigid and more flexible material than the base plate in order to provide a mechanism for distributing weight.

6. The amputation stabilization device as recited in claim 1, wherein the irregular, non-symmetrical shape of the base plate is designed to anatomically match a cross section defined by remaining ends of a partially amputated tibia and fibula so as to not significantly extend past edges of a tibia and fibula when attached thereto.

7. The amputation stabilization device as recited in claim 1, wherein the irregular, non-symmetrical shape of the base plate is designed to extend beyond edges of a tibia and fibula when attached thereto to provide increased lateral surface area to better distribute concentrated loads experienced during walking or running.

8. The amputation stabilization device as recited in claim 1, wherein the second stabilizing component comprises a hollow tube configured to externally cover part of a remaining end of a fibula of a partially amputated leg.

9. The amputation stabilization device as recited in claim 8, wherein the first stabilizing component comprises an intramedullary rod configured to be inserted into an intramedullary bone canal in as tibia of a partially amputated human leg.

10. An amputation stabilization device for mechanically stabilizing a remaining end of a tibia relative to a remaining end of a fibula of a partially amputated leg, the amputation stabilization device comprising:

first means for engaging a remaining end of a tibia of a partially amputated leg, the first means having a distal end and a proximal end;

second means for engaging a remaining end of a fibula of the partially amputated leg, the second means having a distal end and proximal end; and a base plate having a proximal side and a distal side that is substantially flat or curved and substantially free of protrusions, the base plate having a first irregular, non-symmetrically shaped region configured so as to be mechanically connected or connectable to the distal end of the first means and the base plate having a second irregular, non-symmetrically shaped region configured so as to be mechanically connected or connectable to the distal end of the second means, wherein the base plate has an irregular, non-symmetrical shape that at least partially approximates a remaining cross-section of a partially amputated leg;

wherein the first means is configured to extend from the proximal side of the base plate in the first region;

wherein the second means is configured to extend from the proximal side of the base plate in the second region; and wherein during use of the amputation stabilization device the first means has a position on the base plate relative to a position of the second means on the base plate in order to maintain an anatomically correct separation between remaining ends of a tibia and a fibula when the first means and the second means engage the remaining ends of a tibia and a fibula, respectively, and wherein the amputation stabilization device is configured to decrease independent movement of a tibia relative to a fibula of a partially amputated leg during dynamic loading of the partially amputated leg.

11. A dual stem amputation implant for mechanically stabilizing a remaining end of a first bone relative to a remaining end of a second bone of a partially amputated human limb, the dual stem amputation implant comprising:

a first intramedullary rod configured for insertion into a first intramedullary canal of a remaining end of the first bone, the first intramedullary rod having a first diameter based on a first cross-sectional size of the first intramedullary canal of the first bone, the first intramedullary rod having a first threaded end and a first substantially cylindrical portion extending from the first threaded end;

a second intramedullary rod configured for insertion in a second intramedullary canal of a remaining end of the second bone, the second intramedullary rod having a second diameter that is less than the first diameter of the first intramedullary rod based on a second cross-sectional size of the second intramedullary canal of the second bone, the second intramedullary rod having a second threaded end and a second substantially cylindrical portion extending from the second threaded end; and a base plate having a proximal side and a distal side, the base plate being initially separate from the first and second intramedullary rods, the base plate comprising first and second threaded openings configured for receiving the first and second threaded ends, respectively, of the first and second intramedullary rods such that the base plate may be selected from among differently-sized base plates and the first and second intramedullary rods may be selected from among differently-sized intramedullary rods in order to construct an appropriately sized dual stem implant based on a size and/or shape of remaining ends of the first and second bones of a partially amputated human limb, the first threaded opening being formed in a first region of the base plate having a first irregular, non-symmetrical shape that approximates a remaining cross section of the first bone and the second threaded opening being formed a second region of the base plate having a second irregular, non-symmetrical shape that is different than the first shape and that approximates a remaining cross section of the second bone, and wherein the base plate has an irregular, non-symmetrical shape that approximates a remaining cross-section of a partially amputated human limb;

wherein the first intramedullary rod is configured to extend from the proximal side of the base plate;

wherein the second intramedullary rod is configured to extend from the proximal side of the base plate; and wherein during use of the dual stem amputation implant the first intramedullary rod has a position on the base plate relative to a position of second intramedullary rod on the base plate in order to maintain an anatomically correct separation between the remaining ends of the first bone and the second bone when the first intramedullary rod and the second intramedullary rod are inserted into the first intramedullary canal of the first bone and the second intramedullary canal of the second bone, respectively, the maintained separation preventing the remaining ends of the first bone and the second bone from independently moving towards one another during use or loading of the partially amputated human limb.

12. The dual stem implant as recited in claim 11, wherein:

the first intramedullary rod is configured for insertion into an intramedullary bone canal of a remaining end of a radius of a partially amputated human arm; and the second intramedullary rod is configured for insertion into an intramedullary bone canal of a remaining end of an ulna of a partially amputated human arm.

13. The dual stem implant recited in claim 12, wherein the first intramedullary rod has a position and means of mechanical attachment to the base plate configured to allow rotation of the radius and ulna and provide proper biomechanics when a user rotates the user's wrist or forearm.

14. The dual stem amputation implant as recited in claim 9, further comprising:

a polymer or plastic end cap mechanically attached to the distal side of the base plate, the polymer end cap configured to substantially cover the distal side of the base plate and provide a distal surface that is substantially flat or curved and/or substantially free of protrusions, the polymer end cap comprising a more flexible and less rigid material than the base plate in order to provide a mechanism for further distributing a load.

15. A dual stem amputation implant for mechanically stabilizing remaining ends of a tibia and fibula relative to one another in a partially amputated leg, the dual stem amputation implant comprising:

a first intramedullary rod configured for insertion into an intramedullary canal open at a remaining end of a tibia of a partially amputated leg, the first intramedullary rod having a first threaded end with a first diameter;

a second intramedullary rod configured for insertion into a second intramedullary canal open at a remaining end of a fibula of a partially amputated leg, the second intramedullary rod having a second threaded end with a second diameter that is less than the first diameter of the first threaded end; and a base plate having a proximal side and a distal side, the base plate being initially separate from the first and second intramedullary rods, the base plate comprising a first threaded opening configured for threadably receiving the first threaded end of the first intramedullary rod but not the second threaded end of the second intramedullary rod in order to prevent the second threaded end to be screwed into the first threaded opening and the base plate comprising a second threaded opening configured for threadably receiving the second threaded end of the second intramedullary rod but not the first threaded end of the first intramedullary rod in order to prevent the first threaded end to be screwed into the second threaded opening such that the base plate may be selected from among differently sized base plates and the first and second intramedullary rods may be selected from among differently sized intramedullary rods in order to construct an appropriately sized dual stem implant based on a size, shape and/or separation of the distal ends of the tibia and fibula, the first threaded opening being formed in a first region of the base plate having a first irregular, non-symmetrical shape that approximates a remaining cross section of a tibia and the second threaded opening being formed a second region of the base plate having a second irregular, non-symmetrical shape that is different than the first shape and that approximates a remaining cross section of a fibula, and wherein the base plate has an irregular, non-symmetrical shape that approximates a remaining cross-section of a partially amputated leg;

wherein the first intramedullary rod is configured to extend from the proximal side of the base plate and form a non-flared interface with the base plate;

wherein the second intramedullary rod is configured to extend from the proximal side of the base plate and form a non-flared interface with the base plate; and wherein during use of the dual stem amputation implant the first intramedullary rod has a position on the base plate relative to a position of the second intramedullary rod on the base plate in order to maintain an anatomically correct separation between the remaining ends of the tibia and fibula when the first intramedullary rod and the second intramedullary rod are inserted into the first intramedullary canal of the tibia and the second intramudullary canal of the fibula, respectively.

16. The dual stem amputation implant as recited in claim 15, further comprising:

an end cap mechanically attached to the distal side of the base plate, the end cap configured to substantially cover the distal side of the base plate and provide a distal surface that is substantially flat or curved and/or substantially free of protrusions, the end cap comprising a more flexible and less rigid material than the base plate in order to provide a mechanism for further distributing weight.

17. The dual stem amputation implant as recited in claim 16, wherein the end cap comprises a plastic or polymer.

18. The dual stem amputation implant as recited in claim 16, wherein the end cap is configured to match the size and/or shape of the base plate.

19. The dual stem amputation implant as recited in claim 15, wherein the base plate has an irregular, non-symmetrical shape that is configured to anatomically match a cross section of a remaining end of a partially amputated leg so as to not significantly extend past edges of a tibia and fibula when attached thereto.

20. The dual stem amputation implant as recited in claim 15, wherein the base plate has an irregular, non-symmetrical shape that is configured to extend past edges of remaining ends of a tibia and fibula of a partially amputated leg to provide increased lateral surface area so as to better distribute concentrated loads experienced during walking or running

21. The dual stem amputation implant as recited in claim 15, the implant comprising a plurality of differently sized first intramedullary rods, a plurality of differently sized second intramedullay rods, and a plurality of differently-sized base plates from which can be constructed an appropriately sized apparatus based on respective cross-sections of and distance between remaining ends of a tibia and fibula of a partially amputated leg.

22. The dual stem implant as recited in claim 15, wherein the base plate includes a proximal side surface configured to promote bone growth into the base plate.

23. The dual stem implant as recited in claim 15, wherein the distal side of the base plate has a flattened dome shape that is substantially free of protrusions.

24. The dual stem implant as recited in claim 15, wherein the first intramedullary rod has a diameter that is less than a diameter of an intramedullary canal reamed into a tibia to provide space for insertion of bone cement into the intramedullary canal reamed into the tibia.

25. The dual stem implant as recited in claim 15, wherein the second intramedullary rod has a diameter that is less than a diameter of an intramedullary canal reamed into a fibula to provide space for insertion of bone cement into the intramedullary canal reamed into the fibula.

26. The dual stem implant as recited in claim 15, wherein at least one of the first and second intramedullary rods is provided with a surface configured to promote bone growth into the intramedullary rod.

27. The dual stem implant as recited in claim 15, wherein at least one of the first and second intramedullary rods has a substantially circular cross-sectional area.

28. The dual stem implant as recited in claim 15, wherein the first and second intramedullary rods are substantially parallel to each other when attached to the base plate.

29. An amputation stabilization device for mechanically stabilizing remaining ends of a tibia and fibula relative to one another in a partially amputated leg, the dual stem amputation implant comprising:

a first intramedullary rod configured for insertion into an intramedullary canal open at a remaining end of a tibia of a partially amputated leg, the first intramedullary rod having a first threaded end and a first diameter;

a second intramedullary rod configured for insertion into a second intramedullary canal open at a remaining end of a fibula of the partially amputated leg, the second intramedullary rod having a second threaded end and a second diameter that is less than the first diameter of the first intramedullary rod; and a base plate having a proximal side and a distal side, the base plate comprising a first threaded opening through the proximal side configured to receive the first threaded end of the first intramedullary rod and a second threaded opening through the proximal side configured to receive the second threaded end of the second intramedullary rod and exclude the first threaded end of the first intramedullary rod, the distal side of the base plate having a substantially flat or curved surface substantially free of protrusions, the base plate having an irregular, non-symmetrical shape that at least partially approximates a remaining cross-section of a partially amputated leg.

30. The amputation stabilization device as recited in claim 29, wherein the base plate has an irregular, non-symmetrical shape that is designed to extend past edges of a tibia and fibula when attached thereto to provide increased lateral surface area to better distribute concentrated loads experienced during walking or running.

31. The amputation stabilization device as recited in claim 29, wherein the base plate has an irregular, non-symmetrical, anatomical shape that is designed so as to not significantly extend past edges of a tibia and fibula when attached thereto.

* * * * *

UNITED STATES PATENT AND TRADEMARK OFFICE

CERTIFICATE OF CORRECTION

PATENT NO. : 7,972,384 B2
APPLICATION NO. : 12/238108
DATED : July 5, 2011
INVENTOR(S) : Douglas E. Parsell It is certified that error appears in the above-identified patent and that said Letters Patent is hereby corrected as shown below:

On the Title Page, Item 56, References Cited, OTHER PUBLICATIONS, Right Hand Column
After "1490-1497." and before "Bernd," insert a carriage return Column 1
Line 49, change "calf However" to --calf. However--

Column 4
Line 20, before "distal side 136" insert --a--
Line 27, after "etc." insert a space
Line 45, change "corresponds" to --corresponding--

Column 6
Line 35, change "significant" to --significantly--
Line 49, change "steam" to --stem--

Column 7
Line 39, change "principles of the of the present" to --principles of the present--

Column 9
Line 4, after "side" insert --of--
Line 29, change "as" to --a--
Line 40, change "and proximal" to --and a proximal--

Column 11
Line 9, change "claim 9" to --claim 11--

Column 12
Line 12, change "mudullary" to --medullary--
Line 39, change "running" to --running.--

Signed and Sealed this
Twenty-seventh Day of September, 2011

David J. Kappos

David J. Kappos
*Director of the United States Patent and Trademark Office*